US008611551B1

(12) United States Patent
Massie et al.

(10) Patent No.: US 8,611,551 B1
(45) Date of Patent: Dec. 17, 2013

(54) LOW LATENCY ACTIVE NOISE CANCELLATION SYSTEM

(71) Applicants: Dana Massie, Santa Cruz, CA (US); Jean Laroche, Santa Cruz, CA (US)

(72) Inventors: Dana Massie, Santa Cruz, CA (US); Jean Laroche, Santa Cruz, CA (US)

(73) Assignee: Audience, Inc., Mountain View, CA (US)

( * ) Notice: Subject to any disclaimer, the term of this patent is extended or adjusted under 35 U.S.C. 154(b) by 0 days.

(21) Appl. No.: 13/935,847

(22) Filed: Jul. 5, 2013

Related U.S. Application Data

(63) Continuation of application No. 13/493,648, filed on Jun. 11, 2012, now Pat. No. 8,526,628, which is a continuation-in-part of application No. 12/950,431, filed on Nov. 19, 2010.

(60) Provisional application No. 61/286,117, filed on Dec. 14, 2009, provisional application No. 61/495,334, filed on Jun. 9, 2011.

(51) Int. Cl.
*A61F 11/06* (2006.01)

(52) U.S. Cl.
USPC .......... 381/71.1; 381/94.1; 708/313; 341/143

(58) Field of Classification Search
USPC ............... 381/71.1, 71.8, 71.9, 71.11, 17, 92, 381/309, 370, 94.1; 700/94; 341/143–145, 341/120, 126, 150; 708/313
See application file for complete search history.

(56) References Cited

U.S. PATENT DOCUMENTS 5,103,229 A * 4/1992 Ribner .......................... 341/143

* cited by examiner

*Primary Examiner* — Vivian Chin
*Assistant Examiner* — Friedrich W Fahnert
(74) *Attorney, Agent, or Firm* — Carr & Ferrell LLP

(57) ABSTRACT

Systems and methods described herein provide for low latency active noise cancellation, which alleviates the problems associated with analog filter circuitry. The present technology utilizes low latency digital signal processing techniques that overcome the high latency conventionally associated with conversion between the analog and digital domains. As a result, low latency active noise cancellation is performed utilizing digital filter circuitry which is not subject to the inaccuracies and drift of analog filter components. In doing so, the present technology provides robust, high quality active noise cancellation.

20 Claims, 12 Drawing Sheets

LOW LATENCY ACTIVE NOISE CANCELLATION SYSTEM

CROSS-REFERENCE TO RELATED APPLICATIONS

This application is a continuation of U.S. application Ser. No. 13/493,648, filed Jun. 11, 2012, which is a continuation in part (CIP) of U.S. application Ser. No. 12/950,431, filed Nov. 19, 2010, which claims the benefit of U.S. Provisional Application No. 61/286,117, filed Dec. 14, 2009, all of which are incorporated here by reference in their entireties for all purposes. U.S. application Ser. No. 13/493,648 also claims the benefit of U.S. Provisional Application No. 61/495,334, filed Jun. 9, 2011, which is incorporated here by reference in its entirety for all purposes.

BACKGROUND

1. Field of the Invention

The present invention relates generally to audio processing and more particularly to techniques for active noise cancellation.

2. Description of Related Art

An active noise cancellation (ANC) system in an earpiece-based audio device can be used to reduce background noise. The ANC system forms a compensation signal adapted to cancel background noise at a listening position inside the earpiece. The compensation signal is provided to an audio transducer (e.g., a loudspeaker) that generates an "anti-noise" acoustic wave. The anti-noise acoustic wave is intended to attenuate or eliminate the background noise at the listening position via destructive interference, so that only the desired audio remains. Consequently, the combination of the anti-noise acoustic wave and the background noise at the listening position results in cancellation of both and, hence, a reduction in noise.

ANC systems may generally be divided into feedforward ANC systems and feedback ANC systems. In a typical feedforward ANC system, a reference microphone provides a reference signal based on the background noise captured at a reference position. The reference signal is then used by the ANC system to predict the background noise at the listening position so that the background noise can be cancelled. Typically, this prediction utilizes a transfer function which models the acoustic path from the reference position to the listening position. Active noise cancellation is then performed to form a compensation signal adapted to cancel the noise, whereby the reference signal is filtered based on the transfer function.

The performance of the ANC system is constrained by the latency (or delay) introduced during the formation of the compensation signal. The latency limits the amount of noise attenuation achievable by the ANC system. For feedforward systems, excessive latency makes the anti-noise signal arrive too late to effectively cancel the noise signal, resulting in unsatisfactory cancellation at higher frequencies. For feedback systems, excessive latency can cause the closed-loop system to become unstable when the feedback gain is increased, thereby effectively limiting the gain to a small value, which results in degraded noise attenuation performance. In either case, the resulting residual noise can interfere with the listening experience of desired sound and is annoying. In some instances, the latency may result in the generation of an anti-noise acoustic wave that constructively interferes with the background noise at the listening position. In such a case, the combination of the anti-noise acoustic wave and the background noise may result in an increase in the noise at the listening position, rather than a decrease.

In order to achieve a relatively low latency, an ANC system may be implemented using analog filter circuitry. The analog circuitry filters and inverts the analog reference signal received from the reference microphone to form an analog compensation signal, which is then provided to the loudspeaker. Although low latency can be achieved, the use of analog filter circuitry to perform active noise cancellation results in a number of drawbacks. For example, it can be difficult to achieve high precision or accuracy using analog filter components due to component variation. As a result, the component variation limits the overall noise cancellation performance of the ANC system. In addition, analog filter components are susceptible to drift and aging, which can cause the performance to worsen over time. Finally, it can be difficult to change component values to adapt to various situations or to provide the user more flexibility in the amount or the nature of the noise attenuation, which makes analog circuitry less flexible in practice than digital solutions.

It is therefore desirable to provide low latency active noise cancellation techniques that can also address the problems associated with analog filter circuitry.

SUMMARY

Systems and methods described herein provide for low latency active noise cancellation, which alleviates the problems associated with analog filter circuitry. The present technology utilizes low latency digital signal processing techniques which overcome the high latency conventionally associated with conversion between the analog and digital domains. As a result, low latency active noise cancellation is performed utilizing digital filter circuitry which is not subject to the inaccuracies and drift of analog filter components. In doing so, the present technology provides robust, flexible, and high quality active noise cancellation.

A method for reducing an acoustic energy level at a listening position as described herein includes receiving a primary acoustic wave at a reference position to form an analog reference signal. The analog reference signal is converted into a digital reference signal using an oversampling data converter. A digital noise reduction signal is then formed based on the digital reference signal using a filter. The digital reference signal may or may not be processed by a decimator prior to feeding it into the filter. If the decimator is not used or bypassed, then the filter may be specifically configured to receive and process a single-bit data stream. Bypassing the decimator allows further reduction in latency. The digital noise reduction signal is then converted into an analog noise reduction signal. The digital noise reduction signal may be a single-bit stream and may be fed directly into the digital-to-analog converter. A secondary acoustic wave is then generated based on the analog noise reduction signal. The secondary acoustic wave is adapted to reduce the acoustic energy level at the listening position.

A system for reducing an acoustic energy level at a listening position as described herein includes a reference microphone to receive a primary acoustic wave at a listening position. The system also includes a noise cancellation module to convert the analog reference signal into a digital reference signal using an oversampling data converter. The noise cancellation module then uses a specially designed filter to form a digital noise reduction signal based on the single-bit digital reference signal, the filter receiving the single-bit digital reference signal directly from the oversampling data converter. The noise cancellation module may also convert the digital noise reduction signal into an analog noise reduction signal. The system further includes an audio transducer to generate a secondary acoustic wave based on the analog noise reduction signal, with the second acoustic wave adapted to reduce the acoustic energy level at the listening position.

A non-transitory computer readable storage medium as described herein has embodied thereon a program executable by a processor to perform a method for reducing an acoustic energy level at a listening position as described above.

Other aspects and advantages of the present invention can be seen on review of the drawings, the detailed description, and the claims which follow.

DETAILED DESCRIPTION

Systems and methods described herein provide for low latency active noise cancellation, which alleviates the problems associated with analog filter circuitry. The present technology utilizes low latency digital signal processing techniques that overcome the high latency conventionally associated with conversion between the analog and digital domains. As a result, low latency active noise cancellation is performed utilizing digital filter circuitry, which is not subject to the inaccuracies and drift of analog filter components. In doing so, the present technology provides robust, flexible, and high quality active noise cancellation.

Embodiments of the present technology may be practiced on any earpiece-based audio device that is configured to receive and/or provide audio such as, but not limited to, cellular phones, MP3 players, phone handsets, and headsets. While some embodiments of the present technology will be described in reference to operation on a cellular phone, the present technology may be practiced on any audio device.

Figure 1:
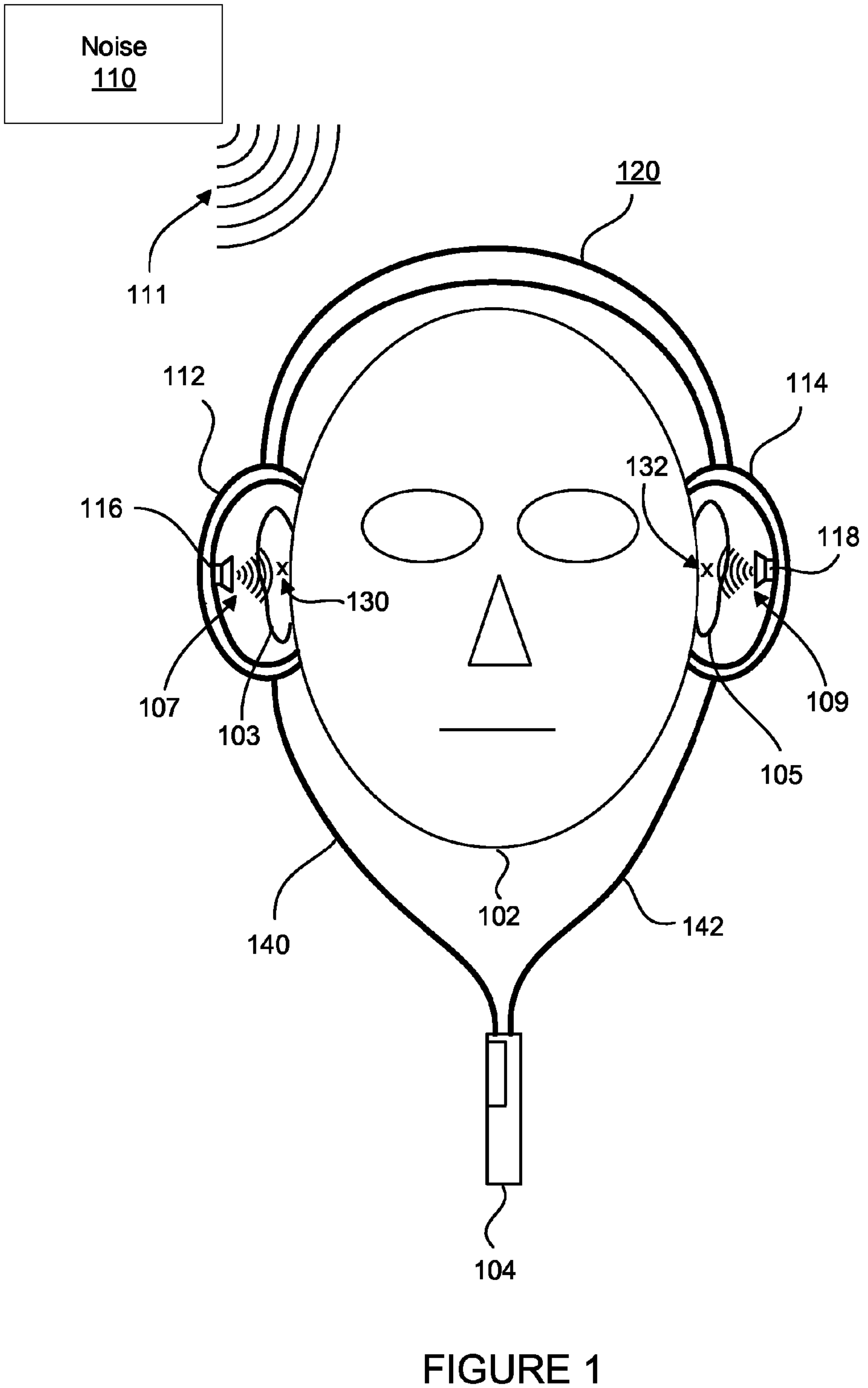
FIG. 1 is an illustration of an environment in which embodiments of the present technology may be used.

FIG. 1 is an illustration of an environment in which embodiments of the present technology may be used. An audio device 104 may act as a source of audio content to a headset 120 which can be worn over or in the ears 103, 105 of a user 102. The audio content provided by the audio device 104 may, for example, be stored on a storage media such as a memory device, an integrated circuit, a CD, a DVD, and the like for playback to the user 102. The audio content provided by the audio device 104 may include a far-end acoustic signal received over a communications network, such as the speech of a remote person talking into a second audio device. The audio device 104 may provide the audio content as mono or stereo acoustic signals to the headset 120 via one or more audio outputs. As used herein, the term "acoustic signal" refers to a signal derived from or based on an acoustic wave corresponding to actual sounds, including acoustically derived electrical signals that represent an acoustic wave.

In the illustrated embodiment, the exemplary headset 120 includes a first earpiece 112 positionable on or in the ear 103 of the user 102, and a second earpiece 114 positionable on or in the ear 105 of the user 102. Alternatively, the headset 120 may include a single earpiece. The term "earpiece" as used herein refers to any sound delivery device positionable on or in a person's ear (such as, for example, an ear bud, headphone, or other speaker mechanism.

The audio device 104 may be coupled to the headset 120 via one or more wires, a wireless link, or any other mechanism for communication of information. In the illustrated embodiment, the audio device 104 is coupled to the first earpiece 112 via wire 140, and is coupled to the second earpiece 114 via wire 142.

The first earpiece 112 includes an audio transducer 116 that generates an acoustic wave 107 proximate the ear 103 of the user 102 in response to a first acoustic signal. The second earpiece 114 includes an audio transducer 118 which generates an acoustic wave 109 proximate the ear 105 of the user 102 in response to a second acoustic signal. Each of the audio transducers 116 and 118 may, for example, be a loudspeaker or any other type of audio transducer that generates an acoustic wave in response to an electrical signal.

As described below, the first acoustic signal includes a desired signal such as the audio content provided by the audio device 104. The first acoustic signal also includes a first noise reduction signal adapted to cancel undesired background noise at a first listening position 130 using the techniques described herein. Similarly, the second acoustic signal includes a desired signal such as the audio content provided by the audio device 104. The second acoustic signal also includes a second noise reduction signal adapted to cancel undesired background noise at a second listening position 132 using the techniques described herein. In some alternative embodiments, the desired signals may be omitted.

As shown in FIG. 1, an acoustic wave (or waves) 111 will also be generated by noise 110 in the environment surrounding the user 102. Although the noise 110 is shown coming from a single location in FIG. 1, the noise 110 may include any sounds coming from one or more locations that differ from the location of the transducers 116, 118 and may include reverberations and echoes. The noise 110 may be stationary, non-stationary, and/or a combination of both stationary and non-stationary noise.

The total acoustic wave at the first listening position 130 is a superposition of the acoustic wave 107 generated by the transducer 116 and the acoustic wave 111 generated by the noise 110. The first listening position 130 may, for example, be in front of the eardrum of ear 103, where the user 102. As described herein, the portion of the acoustic wave 107 due to the first noise reduction signal is configured to destructively interfere with the acoustic wave 111 at the first listening position 130. In other words, the combination of the portion of the acoustic wave 107 due to the first noise reduction signal and the acoustic wave 111 due to the noise 110 at the first listening position 130 results in cancellation of both and, hence, a reduction in the acoustic energy level of noise at the first listening position 130. As a result, the portion of the acoustic wave 107 due to the desired audio signal remains at the first listening position 130.

Similarly, the total acoustic wave at the second listening position 132 is a superposition of the acoustic wave 109 generated by the transducer 118 and the acoustic wave 111 generated by the noise 110. The second listening position 132 may, for example, be in front of the eardrum of the ear 105. Using the techniques described herein, the portion of the acoustic wave 109 due to the second noise reduction signal is configured to destructively interfere with the acoustic wave 111 at the second listening position 132. In other words, the combination of the portion of the acoustic wave 109 due to the second noise reduction signal and the acoustic wave 111 due to the noise 110 at the second listening position 132 results in cancellation of both. As a result, the portion of the acoustic wave 109 due to the desired signal remains at the second listening position 132.

Figure 2:
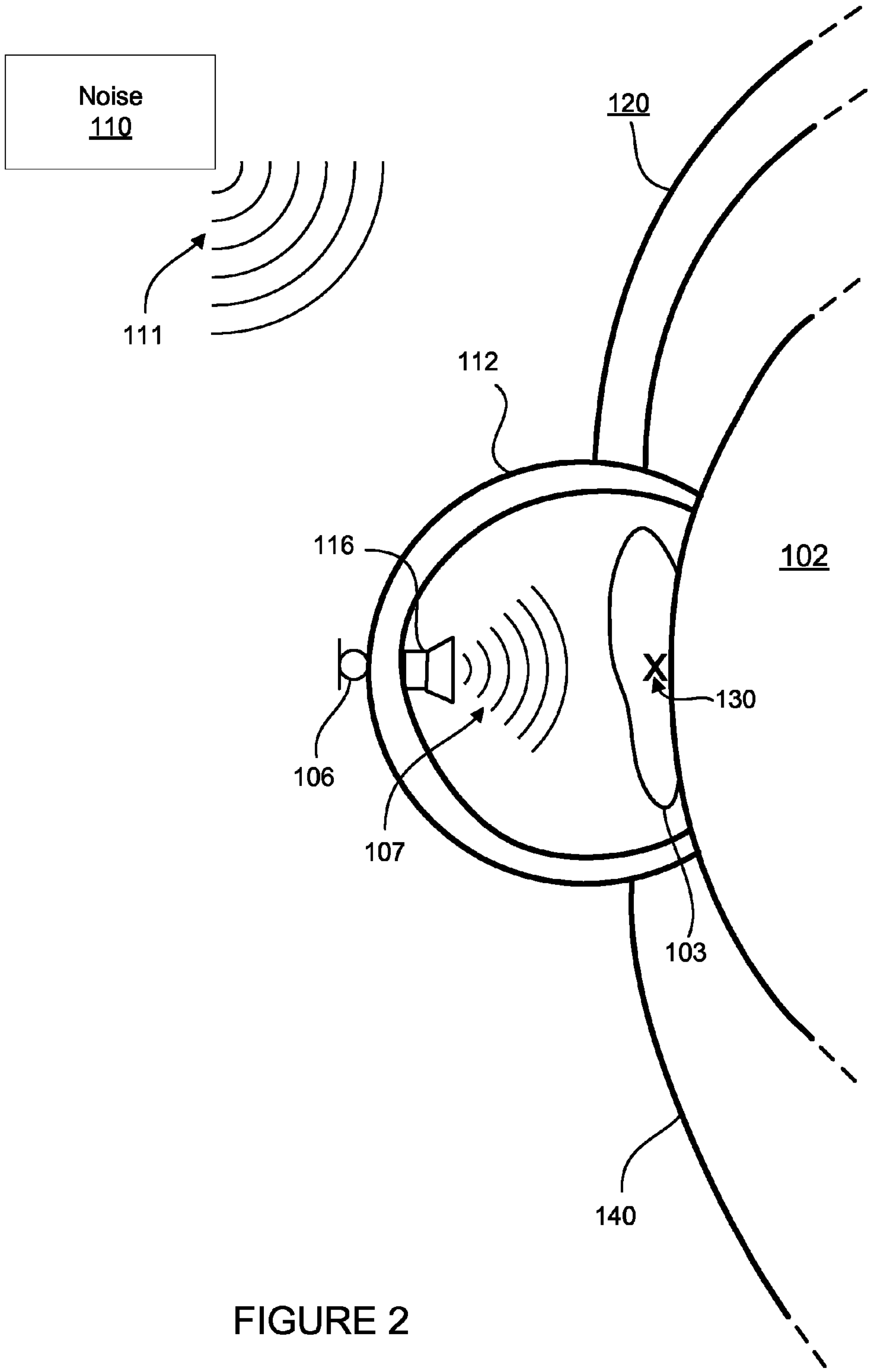
FIG. 2 is an expanded view of an exemplary earpiece of a headset.

The first earpiece 112 is representative of the first and second earpieces 112, 114. FIG. 2 is an expanded view of the first earpiece 112. In the following discussion, ANC techniques are described herein with reference to the first earpiece 112. It will be understood that the techniques described herein can also be extended to the second earpiece 114 to perform active noise cancellation at the second listening position 132.

As shown in FIG. 2, the first earpiece 112 includes a reference microphone 106 at a reference position on the outside of the first earpiece 112. Alternatively, the reference microphone 106 may be positioned within the first earpiece 112.

The acoustic wave 111 due to the noise 110 is received by the reference microphone 106 and converted into an analog reference signal r(t). As used herein, an "analog signal" is a signal whose value at any given moment in time can take on any value within a continuous range of values. As used herein, a "digital signal" is a signal whose value at any given moment in time can take on only a finite number of discrete values within a range of values and which is defined over a discrete set of time samples.

As described below, the analog reference signal r(t) is converted into a decimated digital reference signal R'(n) using an oversampling data converter such as a sigma-delta modulator. The digital reference signal R'(n) is then filtered using a digital filter to form a digital noise reduction signal F'(n). The digital filter is based on a transfer function that models the acoustic path from the location of the reference microphone 106 to the first listening position 130. The transfer function may incorporate characteristics of the acoustic path, such as one or more of an amplitude, phase shift, and time delay from the reference microphone 106 to the first listening position 130. The transfer function can also model the reference microphone 106 response, the transducer 116 response, and the acoustic path from the transducer 116 to the listening position 130.

An analog electric signal g(t), which is formed by converting the digital noise reduction signal F'(n), and optionally a digital desired signal S(n) from the audio device 104, is then provided to the audio transducer 116. In other words, the analog electric signal g(t) is a superposition of an analog noise reduction signal f'(t) corresponding to the digital noise reduction signal F'(n), and an analog desired signal s(t) corresponding to the digital desired signal S(n). Active noise cancellation is then performed at the first listening position 130, whereby the audio transducer 116 generates the acoustic wave 107 in response to the analog electric signal g(t).

Figure 3:
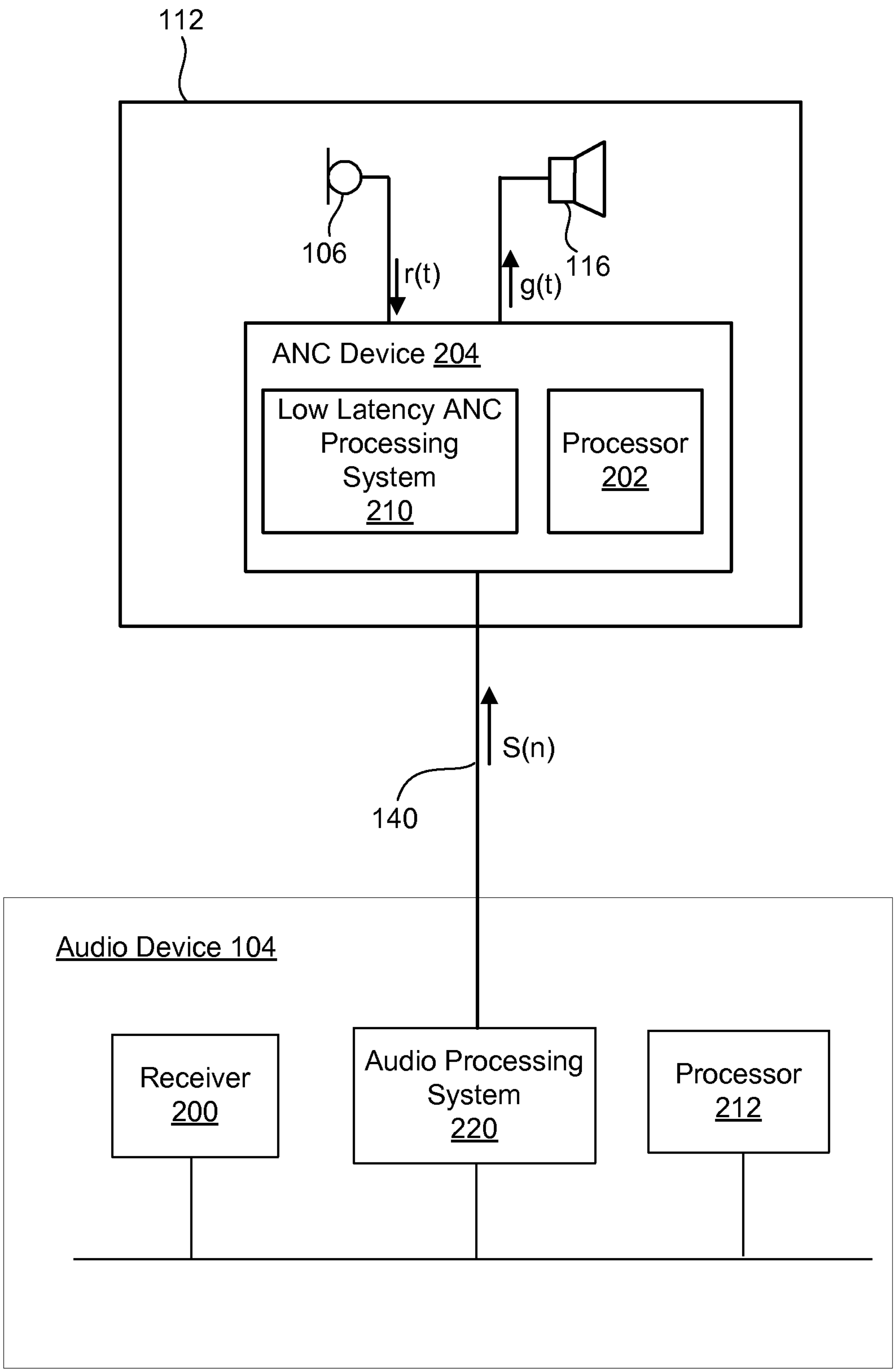
FIG. 3 is a block diagram of an exemplary audio device coupled to an exemplary earpiece of the headset.

FIG. 3 is a block diagram of an exemplary audio device 104 coupled to an exemplary first earpiece 112 of the headset 120. In the illustrated embodiment, the audio device 104 is coupled to the first earpiece 112 via wire 140. The audio device 104 may be coupled to the second earpiece 114 in a similar manner. Alternatively, other mechanisms may be used to couple the audio device 104 to the headset 120.

In the illustrated embodiment, the audio device 104 includes a receiver 200, a processor 212, and an audio processing system 220. The audio device 104 may further include additional or other components necessary for operation of the audio device 104. Similarly, the audio device 104 may include fewer components that perform similar or equivalent functions to those depicted in FIG. 3. In some embodiments, the audio device 104 includes one or more microphones and/or one or more output devices.

Processor 212 may execute instructions and modules stored in a memory (not illustrated in FIG. 3) in the audio device 104 to perform various operations. Processor 212 may include hardware and software implemented as a processing unit, which may process floating operations and other operations for the processor 212.

The exemplary receiver 200 is configured to receive a signal from a communications network. In some embodiments, the receiver 200 may comprise an antenna device. The signal may then be forwarded to the audio processing system 220, and provided as audio content to the user 102 via the headset 120 in conjunction with active noise cancellation as described herein.

The audio processing system 220 is configured to provide desired audio content to the first earpiece 112 in the form of digital desired audio signal S(n). Similarly, the audio processing system 220 is configured to provide desired audio content to the second earpiece 114 in the form of a second digital desired audio signal (not illustrated). The audio content may be retrieved, for example, from data stored on a storage media such as a memory device, an integrated circuit, a CD, a DVD, and the like for playback to the user 102. The audio content may include a far-end acoustic signal received over a communications network, such as the speech of a remote person talking into a second audio device. The desired audio signals may be provided as mono or stereo signals.

An example of the audio processing system 220 in some embodiments is disclosed in U.S. patent application Ser. No. 12/832,920 filed on Jul. 8, 2010 and entitled "Multi-Microphone Robust Noise Suppression," which is incorporated herein by reference.

The exemplary earpiece 112 includes the reference microphone 106, transducer 116, and ANC device 204. In some embodiments, more than two monitoring microphones may be used.

The ANC device 204 includes processor 202 and ANC processing system 210. The processor 202 may execute instructions and modules stored in a memory (not illustrated in FIG. 3) in the ANC device 204 to perform various operations, including low latency active noise cancellation as described herein.

The ANC processing system 210 is configured to receive the reference signal r(t) from the reference microphone 106 and process the signal. Processing includes performing active noise cancellation as described herein. The ANC processing system 210 is discussed in more detail below.

In the illustrated embodiment, the ANC techniques are carried out by the low latency ANC processing system 210 of the ANC device 204. Thus, in the illustrated embodiment, the ANC processing system 210 includes resources to form the digital noise reduction signal F'(n) used to perform active noise cancellation. Alternatively, in some embodiments, the digital noise reduction signal F'(n) may be formed using resources within the audio processing system 220 of the audio device 104.

Figure 4:
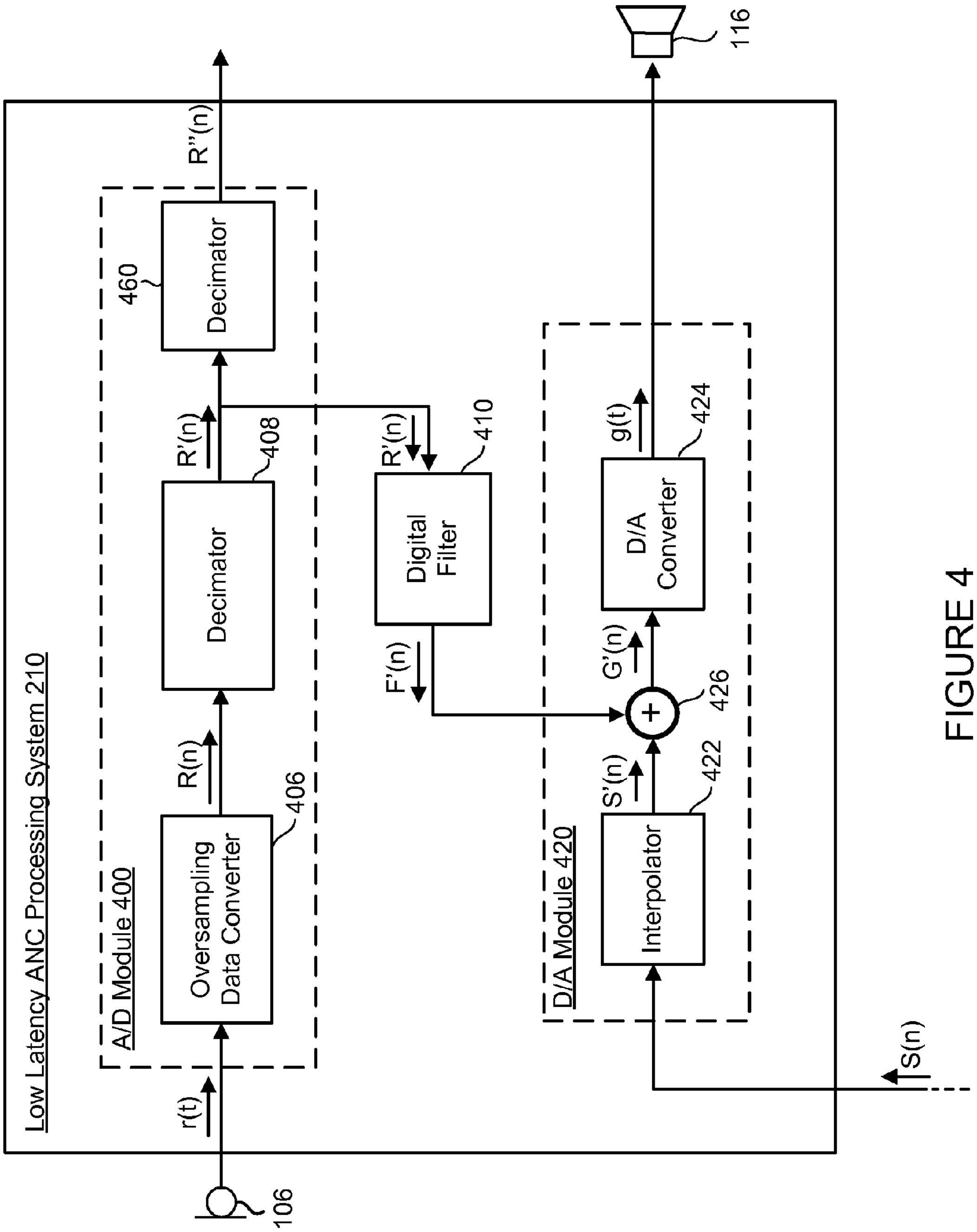
FIG. 4 is a block diagram of an exemplary low latency ANC processing system for performing active noise cancellation as described herein.

FIG. 4 is a block diagram of an exemplary low latency ANC processing system 210 for performing active noise cancellation as described herein. In exemplary embodiments, the low latency ANC processing system 210 is embodied within a memory device within the ANC device 204.

The low latency ANC processing system 210 may include analog-to-digital converter (A/D) module 400, digital filter 410, and digital-to-analog converter (D/A) module 420. The low latency ANC processing system 210 may include more or fewer components than those illustrated in FIG. 4, and the functionality of modules may be combined or expanded into fewer or additional modules. Exemplary lines of communication are illustrated between various modules of FIG. 4 and in other figures herein. The lines of communication are not intended to limit which modules are communicatively coupled with others, nor are they intended to limit the number and type of signals communicated between modules.

In operation, the analog reference signal r(t) generated by the reference microphone 106 is provided to oversampling data converter 406 within the A/D module 400. The oversampling data converter 406 converts the analog reference signal r(t) into a digital reference signal R(n) at a first sampling rate. In the illustrated embodiment, the digital reference signal R(n) is a one-bit data stream at a sampling rate of 3.027 MHz or 2.288 MHz. Alternatively, other sampling rates and numbers of bits may be used.

As used herein, an "oversampling data converter" is an analog-to-digital converter with a sampling rate higher than the target sample rate (such as, for example, by a factor between 8 and 512). In other words, there exist multiple samples of signal R(n) for each sample of signal R'(n).

In the illustrated embodiment, the oversampling data converter 406 is a sigma-delta modulator. Alternatively, other types of data converters may be used for oversampling applications, such as a flash converter.

The digital reference signal R(n) is provided to decimator module 408, hereinafter also referred to as a decimator. The decimator module 408 downsamples the digital reference signal R(n) to produce a decimated digital reference signal R'(n) at a second sampling rate less than the first sampling rate. In other words, the decimator module 408 downsamples the digital reference signal R(n) by a predetermined downsampling factor (decimation factor) to form the decimated digital reference signal R'(n). In the illustrated embodiment, the decimated digital reference signal R'(n) has a sampling rate between 100 and 800 KHz. The decimator module 408 is described in more detail below with respect to FIG. 5.

The decimated digital reference signal R'(n) is then filtered by digital filter 410 to form the digital noise reduction signal F'(n). The digital filter 410 is based on a transfer function which models the acoustic path from the location of the reference microphone 106 to the first listening position 130. The transfer function may incorporate characteristics of the acoustic path, such as one or more of an amplitude, phase shift, and time delay, from the reference microphone 106 to the first listening position 130. The transfer function can also model the reference microphone 106 response, the transducer 116 response, and the acoustic path, e.g. for feedforward ANC, from the transducer 116 to the listening position 130.

The parameter values of the digital filter 410 may, for example, be determined empirically through calibration. The parameter values (e.g., filter gain and cutoff frequency) of the digital filter 410 may, for example, be adjusted from time to time. This adjustment may, for example, be in response to a feedback signal, as described in more detail below with reference to FIG. 8. In such a case, the parameter values may, for example, be stored in the form of a look-up table stored in the memory within the ANC device 204. As another example, the parameter values may be stored in the form of an approximate function derived based on the calibration measurements.

The decimated digital reference signal R'(n) is also provided to optional decimator module 460. The decimator module 460 further downsamples decimated digital reference signal R'(n) to produce decimated digital reference signal R"(n) at the target sampling rate. In the illustrated embodiment, the decimator module 460 comprises a multi-stage half-band infinite impulse response (IIR) decimator. The decimation factor may be, for example, between 2, 4, and 8.

The D/A module 420 receives the digital noise reduction signal F'(n). The D/A module 420 also receives the digital desired signal S(n) from the audio device 104. An interpolator module 422, hereinafter also referred to as an interpolator, within the D/A module 420 "interpolates" the digital desired signal S(n) by upsampling its sampling rate to form interpolated digital desired signal S'(n).

Combiner 426 then combines the digital noise reduction signal F'(n) with the interpolated digital desired signal S'(n) to form combined digital signal G'(n). The combined digital signal G'(n) is then provided to the D/A converter 424. The D/A converter 424 converts the digital output of the combiner 426 into an analog electric signal g(t). The analog electric signal g(t) is then provided to the audio transducer 116. Active noise cancellation is then performed at the first listening position 130, whereby the audio transducer 116 generates the acoustic wave 107 in response to the analog electric signal g(t).

The latency introduced during decimation and interpolation of digital signals can be substantial. The present technology provides low latency ANC by decimating the digital reference signal R(n) to a sampling rate for the decimated digital reference signal R'(n) that is greater than the Nyquist sampling rate. As a result, the latency introduced by the decimation of the digital reference signal R(n) can be significantly less than the latency introduced if the digital reference signal R(n) were decimated down to the Nyquist sampling rate. In addition, by maintaining a relatively high sampling rate in the decimated digital reference signal R'(n), the digital noise reduction signal F'(n) 'bypasses' the interpolation performed by the interpolator module 422. As a result, the latency that would be introduced by the interpolator module 422 is avoided altogether. In doing so, in embodiments, the latency of the ANC device 204 between receiving the primary acoustic wave 111 and generating the secondary acoustic wave 107 can be less than or equal to 100 microseconds. In some embodiments, this latency can be less than or equal to 50 microseconds.

Figure 5:
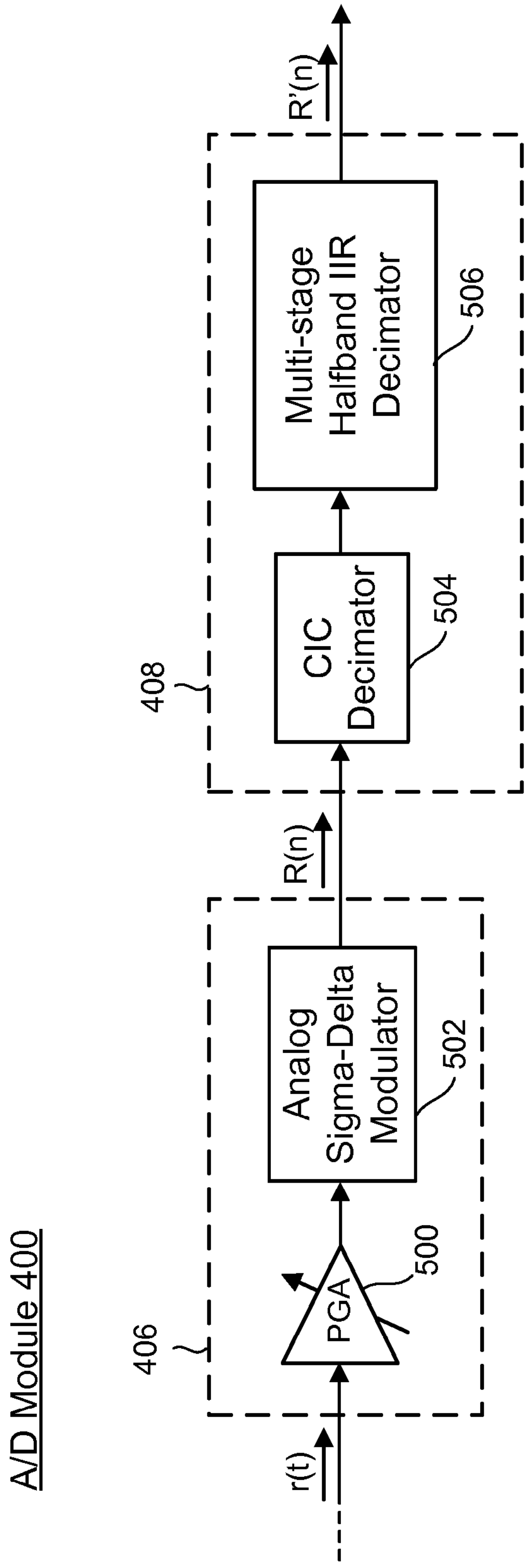
FIG. 5 is a block diagram of an exemplary analog-to-digital converter module.

FIG. 5 is a block diagram of an exemplary A/D module 400. The oversampling data converter 406 may include a pre-gain amplifier (PGA) 500 and an analog sigma-delta modulator 502. The decimator module 408 may include a cascaded integrated comb (CIC) decimator 504 and a multi-stage half-band IIR decimator 506. The oversampling data converter 406 and the decimator module 408 may each include more or fewer components than those illustrated in FIG. 5, and the functionality of modules may be combined or expanded into fewer or additional modules.

The PGA 500 applies a gain to the analog reference signal r(t). The output of the PGA 500 is provided to the analog sigma-delta modulator 502. The analog sigma-delta modulator 502 converts the weighted analog reference signal r(t) into the digital reference signal R(n) at a first sampling rate. The digital reference signal R(n) is a sigma-delta modulator data stream which is typically a one-bit or very small number of bits data stream. As a result, it can be difficult to perform signal processing operations such as filtering directly on the digital reference signal R(n). In particular, various signal processing techniques such as filtering first require conversion of the sigma-delta modulator data stream into a multi-bit pulse-code modulation (PCM) data stream. As described in more detail below, this conversion is performed by the decimator module 408. Specifically, the decimator module 408 both downsamples the digital reference signal R(n) and also generates a multi-bit PCM data stream on which subsequent signal processing steps can then be performed.

The CIC decimator 504 then downsamples the digital reference signal R(n) by a first decimation factor. The first decimation factor may be, for example, between 1 and 32. The weighted multi-stage half-band IIR decimator 506 then further decimates the output of the CIC decimator 504 by a second decimation factor to form the decimated digital reference signal R'(n). The second decimation factor may be, for example, between 2 and 4. The CIC decimator 504 is advantageous because it provides a very high sample rate, and it is also inexpensive. However, the frequency response of the CIC decimator 504 typically is not sufficient for forming a high quality final audio signal at the target sample rate. Including the IIR decimator 506 after the CIC decimator 504, at a lower (cheaper in MIPS) rate, can provide a higher quality overall frequency response for the final signal. In alternative embodiments, the decimator module 408 may be different than that illustrated in FIG. 5. For example, other types of FIR decimation filters may be used at the highest rate by exploiting the fact that the incoming sigma-delta modulator data stream is typically only one bit. In such a case, a one bit multiplier can be implemented as an adder/subtractor combined with a simple table lookup for the polyphase coefficients. In preferred embodiments, an IIR halfband decimator may be used since it provides very low latency as well as a very low implementation cost in terms of memory and MIPS.

Figure 6:
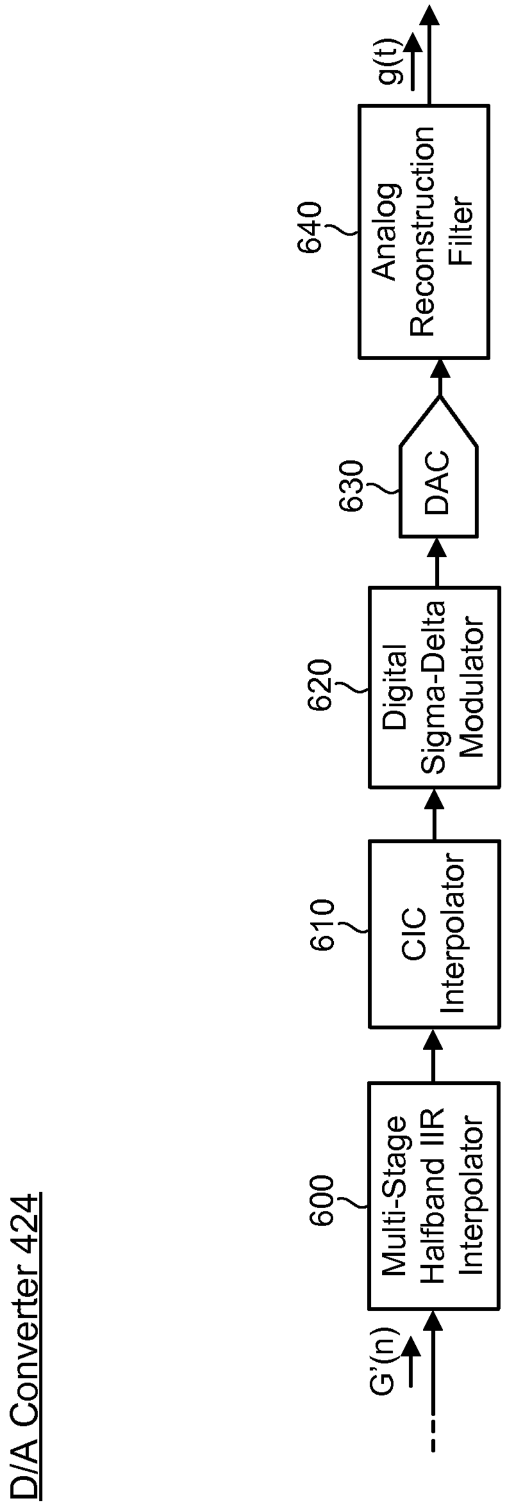
FIG. 6 is a block diagram of an exemplary digital-to-analog converter module.

FIG. 6 is a block diagram of an exemplary D/A converter 424. The D/A converter 424 may include more or fewer components than those illustrated in FIG. 6, and the functionality of modules may be combined or expanded into fewer or additional modules.

The combined digital signal G'(n) is provided to a multi-stage half-band IIR interpolator 600. The multi-stage half-band IIR interpolator 600 interpolates the combined digital signal G'(n) by upsampling its sampling rate by a first interpolation factor. The first interpolation factor may, for example, be 4. CIC interpolator 610 then further interpolates the output of the multi-stage half-band IIR interpolator 600 by a second interpolation factor. The second interpolation factor may be, for example, between 1 and 32.

Digital sigma-delta module 620 then quantizes (i.e., reduces the number of bits) the digital output of the CIC interpolator 610 and shapes the quantization noise. Digital-to-analog converter (DAC) 630 then converts the digital output of the CIC interpolator 610 into a corresponding analog signal. The analog signal is then filtered by analog reconstruction filter 640 to form the analog electric signal g(t).

Figure 7:
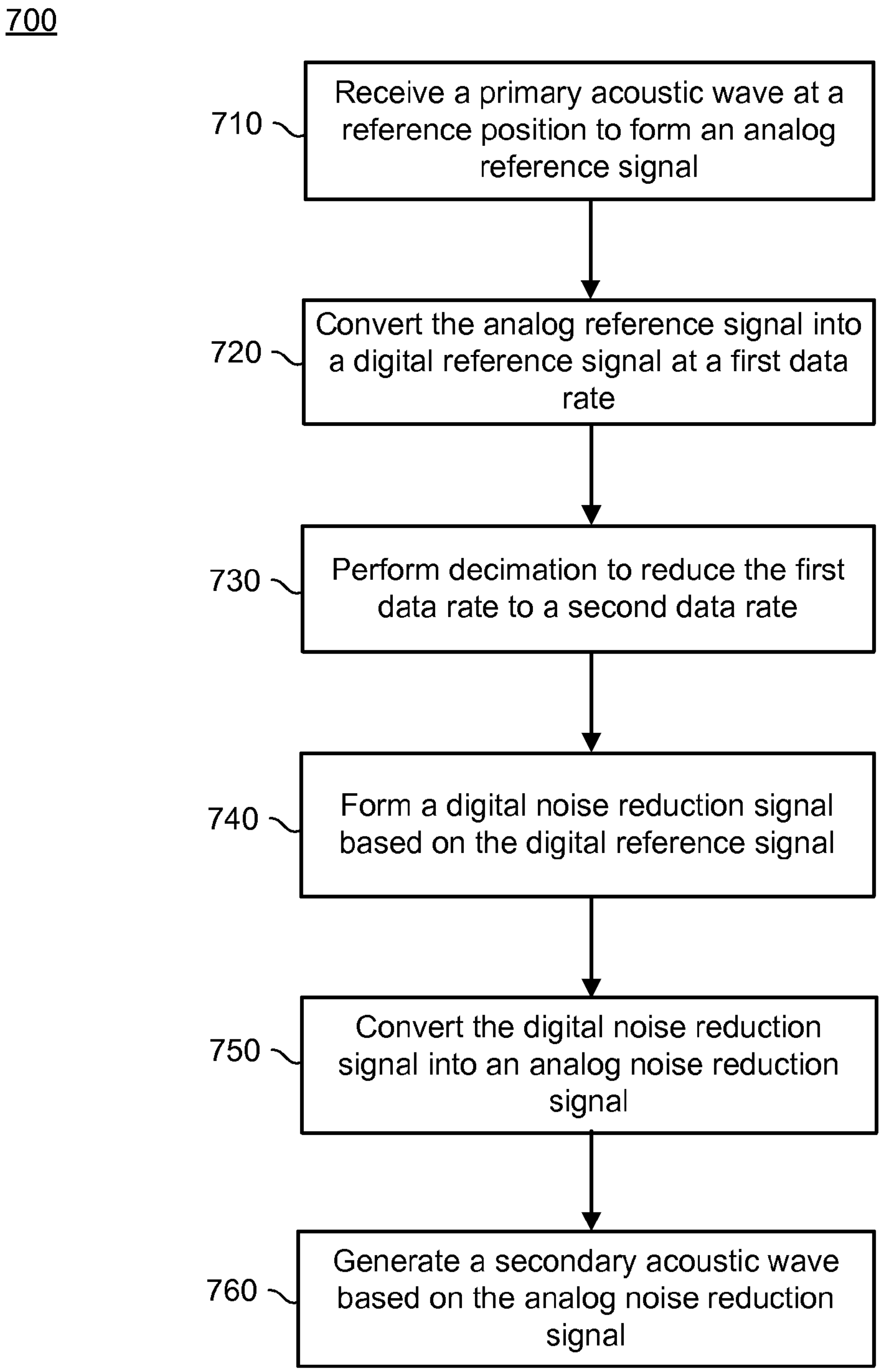
FIG. 7 is a flow chart of an exemplary method for performing active noise cancellation.

FIG. 7 is a flow chart of an exemplary method 700 for performing active noise cancellation. As with all flow charts herein, in some embodiments, the steps may be combined, performed in parallel, or performed in a different order. The method 700 of FIG. 7 may also include more or fewer steps than those illustrated.

In step 710, the primary acoustic wave 111 is received by the reference microphone 106 to form analog reference signal r(t). In some embodiments, more than one reference signal may be received and processed.

In step 720, the analog reference signal r(t) is converted into the digital reference signal R(n) using the oversampling data converter 406. In step 730, decimation is performed on the digital reference signal R(n) to form decimated digital reference signal R'(n).

In step 740, the digital noise reduction signal F'(n) is formed by applying the digital filter 410 to the decimated digital reference signal R'(n). In step 750, the digital noise reduction signal F'(n) is converted into an analog noise reduction signal to form analog electric signal g(t). In step 760, the analog electric signal g(t) is then provided to the transducer 116 of the first earpiece 112 of the headset 120 to generate the secondary acoustic wave 107, thereby performing active noise cancellation at the first listening position 130.

Figure 8:
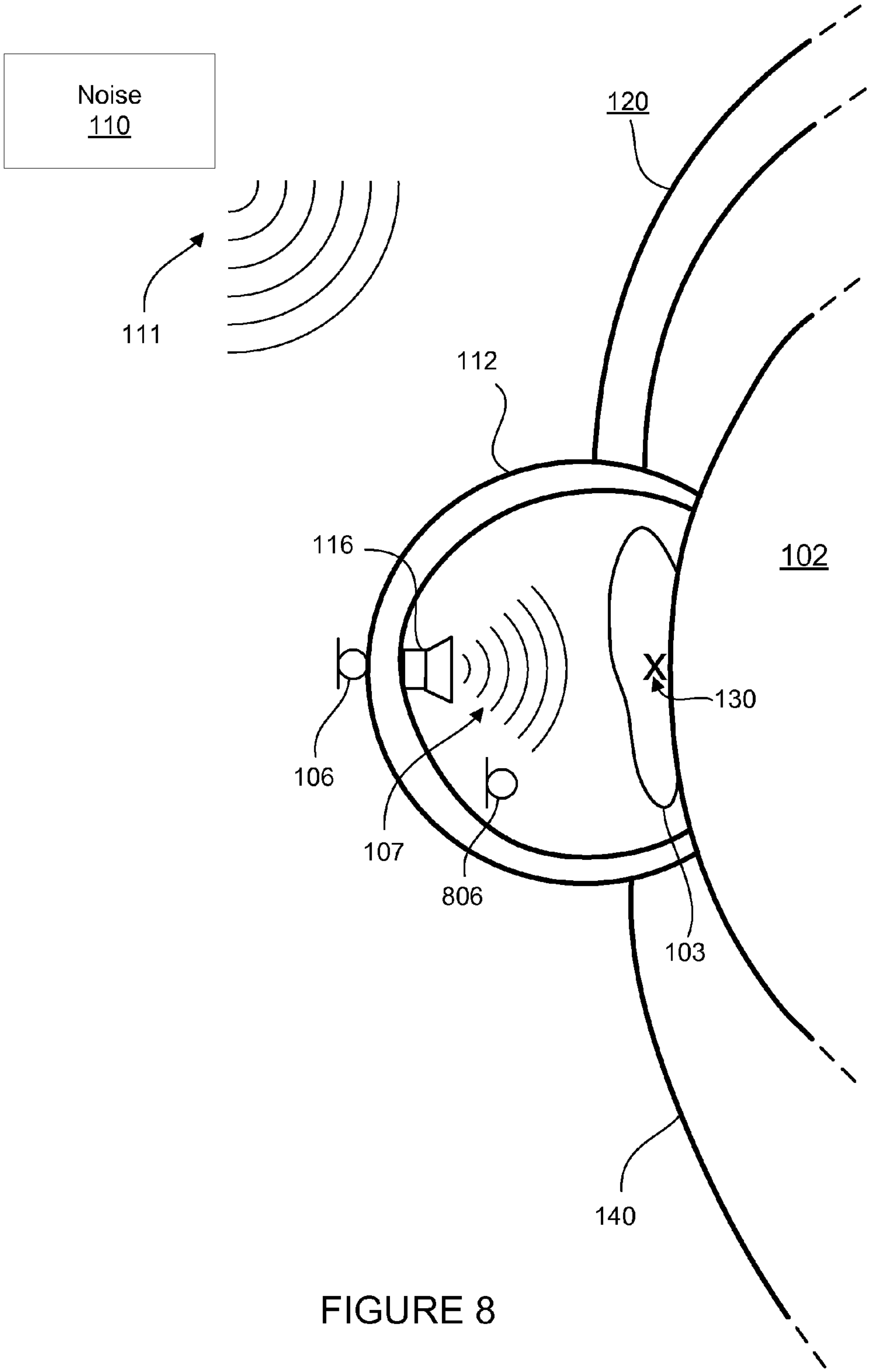
FIG. 8 is an expanded view of a second exemplary earpiece of a headset.

FIG. 8 illustrates an expanded view of the first earpiece 112 that includes a monitoring microphone 806 which can be utilized to perform active noise cancellation as described herein. As shown in FIG. 8, the monitoring microphone 806 is located at a monitoring position within the earpiece 112. The signal received by the monitoring microphone 806 is referred to as monitoring signal m(t). Due to the position of the monitoring microphone 806 within the earpiece 112, the monitoring signal m(t) indicates the acoustic energy level within the earpiece 112.

The monitoring signal m(t) can then be utilized by the ANC device 204 to adjust the parameters (e.g., filter gain and cutoff frequency) of the digital filter 410 used to form the digital noise reduction signal F'(n). By adjusting the digital filter 410 based on the monitoring signal m(t), the digital noise reduction signal F'(n) can be adjusted so as to optimize noise cancellation at the first listening position 130. By doing so, the ANC techniques described herein can achieve optimal noise cancellation in diverse and dynamic acoustic environments.

The monitoring signal m(t) can also be used in lieu of the signal r(t) provided by microphone 106 (FIG. 4) as the input to the A/D module 400. This is the case for a purely feedback ANC system. The digital filter 410 must then have as high a gain as possible, while keeping the closed-loop system stable in all conditions. In addition, it is possible to combine both microphone inputs m(t) and r(t) in a mixed feedforward/feedback technique that includes two filtering blocks (one that implements the feedforward part of the processing, and one that implements the feedback part of the processing).

In some embodiments, a decimation stage may be entirely bypassed, in which case the active noise cancellation algorithm is performed at the sampling rate produced by the oversampling data converter (e.g., the highest sample rate). This approach may be referred as bit-stream processing since the filter is fed with a single-bit data stream produced by the converter. For purposes of this document, the single bit data stream is a data stream that has fewer than eight bits (e.g., one bit, two bits, three bits). This data stream is usually fed at a higher sample rate, which may be between about 1 MHz and 40 MHz or, more specifically, between about 2 MHz and 20 MHz. While one or more decimators may be still included in the A/D module 400, these decimators are not used for streams fed into the active noise cancellation filter.

This approach is different from other embodiments described above, in which a decimator is used to downsample the stream generated by the oversampling data converter. This downsampling may use several sample rate conversion stages and yield multi-bit data (e.g., 8, 16, 24 bits) as described above. This multi-bit data used in other approaches should be distinguished from the single-bit data stream described herein. Bypassing the decimator in this approach allows substantial reduction in latency, and levels of less than 10 microseconds, and even less than 1 microsecond, may be achievable in some embodiments. As such, digital noise cancellation signals provided herein are more comparable (in terms of latency) with analog cancellations systems currently used in noise cancelling headphones and other similar applications. However, digital noise cancellation approaches provide more flexibility and functionality than traditional analog systems.

Overall, various active noise cancellation algorithms are performed directly on single-bit audio streams produced by the oversampling data converter without any initial decimation. The output of these algorithms is also provided as a single bit audio stream, or it is converted into a single-bit audio stream. This resulting single-bit stream algorithm is then sent to the high sample-rate D/A converter or, more specifically, to its digital sigma-delta modulator.

Figure 9A:
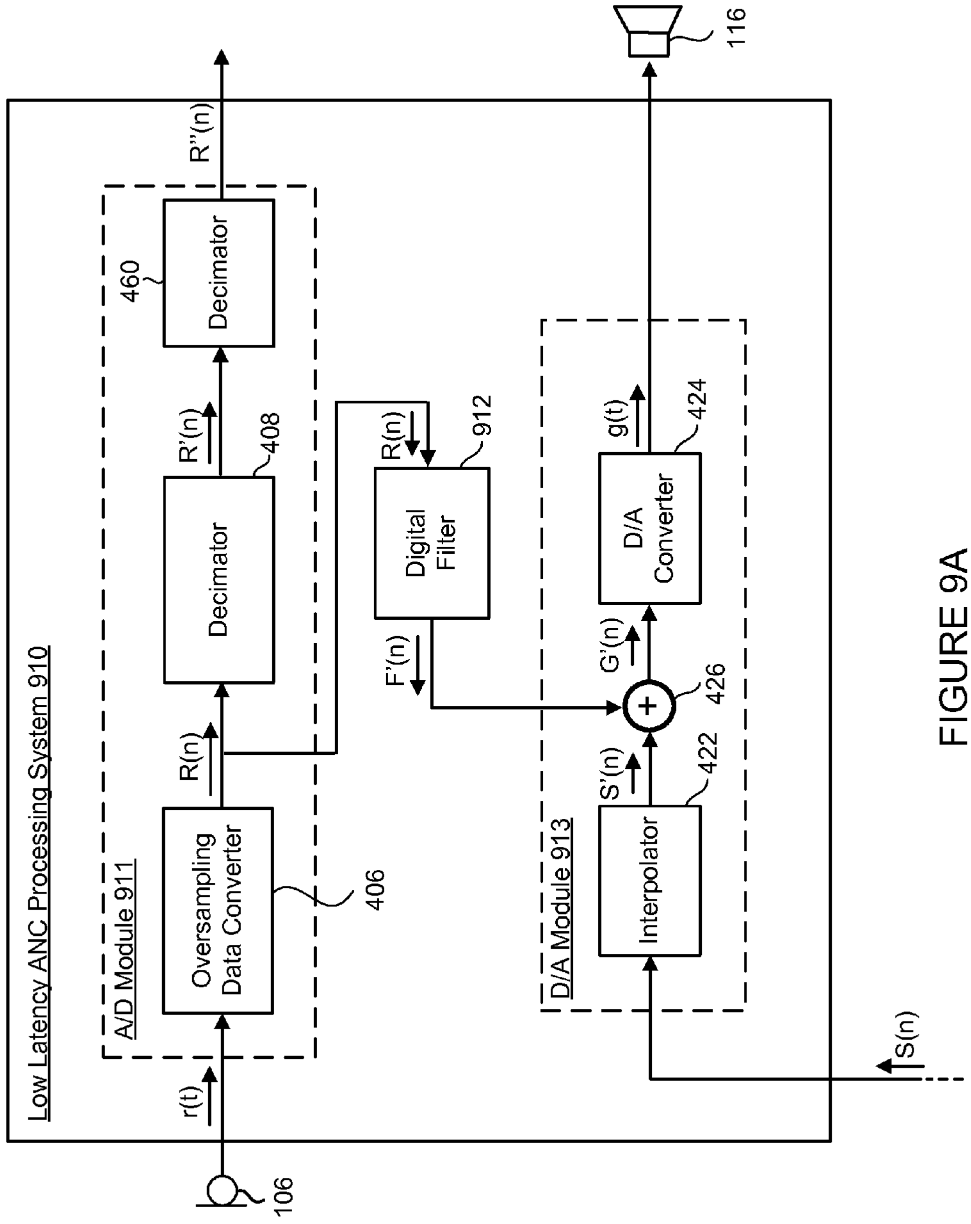
FIG. 9A is a block diagram of another example of a low latency ANC processing system for performing active noise cancellation.

FIG. 9A is a block diagram of a low latency ANC processing system 910 for performing active noise cancellation, in accordance with certain embodiments. This system 910 may be a part of a memory device within the ANC device 204 described above. The low latency ANC processing system 910 may include A/D module 911, digital filter 912, and D/A module 913. The low latency ANC processing system 910 may include more or fewer components than those illustrated in FIG. 9A, and the functionality of modules may be combined or expanded into fewer or additional modules. Exemplary lines of communication are illustrated between various modules of FIG. 9A, and in other figures herein. The lines of communication are not intended to limit which modules are communicatively coupled with others, nor are they intended to limit the number and type of signals communicated between modules.

Some components of the low latency ANC processing system 910 may be the same as components of the low latency ANC processing system described above with reference to FIG. 4. For example, both low latency ANC processing systems may use the same or similar oversampling data converter 406, decimators 408 and 460, interpolator 422, and D/A converter 424. However, the digital filter 912 of the low latency ANC processing system 910 is generally different from various digital filters described above with reference to FIG. 4. As described above, the digital filter 912 takes a single-bit data stream as its input. The digital filter 912 may also produce a single-bit stream as its output. Some processing within the digital filter 912 is performed at a multi-bit level. However, this multi-bit processing may be completely internal to the digital filter 912.

Furthermore, even though some components of the two low latency ANC processing systems (one described above with reference to FIG. 4 and one described here with reference to FIG. 9A) are the same or similar, these components may have different connections and may provide output and/or receive input to and from different components and/or in a different manner. In the low latency ANC processing system 910, the digital filter 912 receives its input directly from the oversampling data converter 406 (and not from the decimator 408). The decimator 408 is effectively bypassed by the single-bit data stream involved in the active noise cancellation operation, thereby reducing the latency.

Some operations performed by the two processing systems (i.e., presented in FIGS. 4 and 9A) are the same, while others are different. For completeness, all operations are described herein. During operation, the analog reference signal r(t) generated by the reference microphone 106 is provided to oversampling data converter 406 within the A/D module 911. The oversampling data converter 406 converts the analog reference signal r(t) into a digital reference signal R(n) at a first sampling rate. In some embodiments, the digital reference signal R(n) is a single-bit data stream at a sampling rate of 3.027 MHz or 2.288 MHz or other sampling rates. For example, the sampling rate may vary between 1 MHz and 40 MHz or, more specifically, between 2 MHz and 20 Mhz. As stated above, the single-bit data stream includes less than eight bits (e.g., one bit, two bits, and three bits).

The digital reference single-bit signal R(n) is provided directly to the digital filter 912 for active noise cancellation processing. The digital reference single-bit signal R(n) may be also provided to the decimator module 408 as a separate stream for different processing. The decimator module 408 downsamples the digital reference signal R(n) to produce a decimated digital reference signal R'(n) at a second sampling rate of less than the first sampling rate. The decimated digital reference signal R'(n) may be then provided to an optional second decimator module 460. The second decimator module 460 further downsamples decimated digital reference signal R'(n) to produce decimated digital reference signal R"(n) at the target sampling rate. In some embodiments, the second decimator module 460 includes a multi-stage half-band IIR decimator. The decimation factor may be, for example, between 2, 4, and 8.

The digital reference single-bit signal R(n) is filtered by the digital filter 912 to form the digital noise reduction signal F'(n). Operations of the digital filter 912 may be based on a transfer function, which models the acoustic path from the location of the reference microphone 106 to the first listening position 130. The parameter values of the digital filter 912 may, for example, be determined empirically through calibration and may be periodically adjusted. This adjustment may, for example, be in response to a feedback signal. In such a case, the parameter values may, for example, be stored in the form of a look-up table stored in the memory within the ANC device 204. As another example, the parameter values may be stored in the form of an approximate function derived based on the calibration measurements. Some of these features may be similar to the features of digital filters described above with reference to FIG. 4. However, digital filter 912 is different in that it receives a single-bit stream as its input and may produce a single-bit stream as its output.

The D/A module 913 receives the digital noise reduction signal F'(n). As stated above, this signal may also be single-bit. The D/A module 913 also receives the digital desired signal S(n) from the audio device 104. An interpolator module 422 within the D/A module 913 may be used to interpolate the digital desired signal S(n) by upsampling its sampling rate to form interpolated digital desired signal S'(n).

Combiner 426 then combines the digital noise reduction signal F'(n) with the interpolated digital desired signal S'(n) to form combined digital signal G'(n). The combined digital signal G'(n) is then provided to the D/A converter 424. The D/A converter 424 converts the digital output of the combiner 426 into an analog electric signal g(t). The analog electric signal g(t) is then provided to the audio transducer 116. Active noise cancellation is then performed at the first listening position 130, whereby the audio transducer 116 generates the acoustic wave 107 in response to the analog electric signal g(t).

Figure 9B:
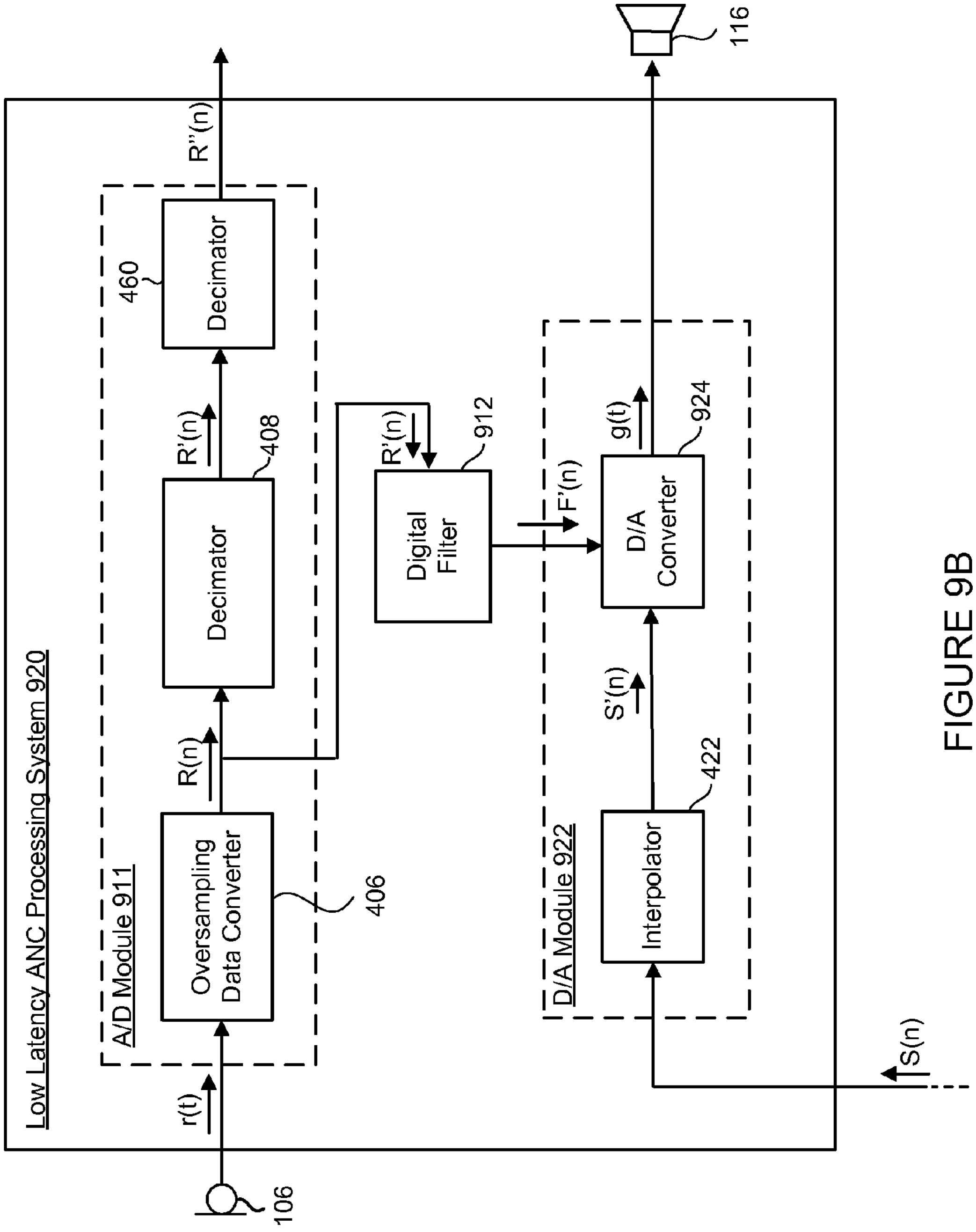
FIG. 9B is a block diagram of yet another example of a low latency ANC processing system for performing active noise cancellation.

The latency introduced during decimation and interpolation of digital signals can be substantial. The low latency ANC processing system 910 described above reduces this latency by eliminating the decimation operation and filtering the single-bit data directly instead. Additional reduction of latency can be achieved by eliminating some interpolation operations at the D/A module level, as will now be explained with reference to FIG. 9B. Specifically, FIG. 9B is a block diagram of another low latency ANC processing system 920 for performing active noise cancellation, in accordance with certain embodiments. This system 920 may be a part of a memory device within the ANC device 204 described above.

The low latency ANC processing system 920 may include A/D module 911, digital filter 912, and D/A module 922. The A/D module 911 and digital filter 912 may be the same or similar as in the system described above with reference to FIG. 9A. The D/A converter module 922 may have different components and interact differently with the digital filter 912 as further described below. The low latency ANC processing system 920 may include more or fewer components than those illustrated in FIG. 9B, and the functionality of modules may be combined or expanded into more or fewer modules. Exemplary lines of communication are illustrated between various modules of FIG. 9B, and in other figures herein. The lines of communication are not intended to limit which modules are communicatively coupled with others, nor are they intended to limit the number and type of signals communicated between modules.

Figure 9C:
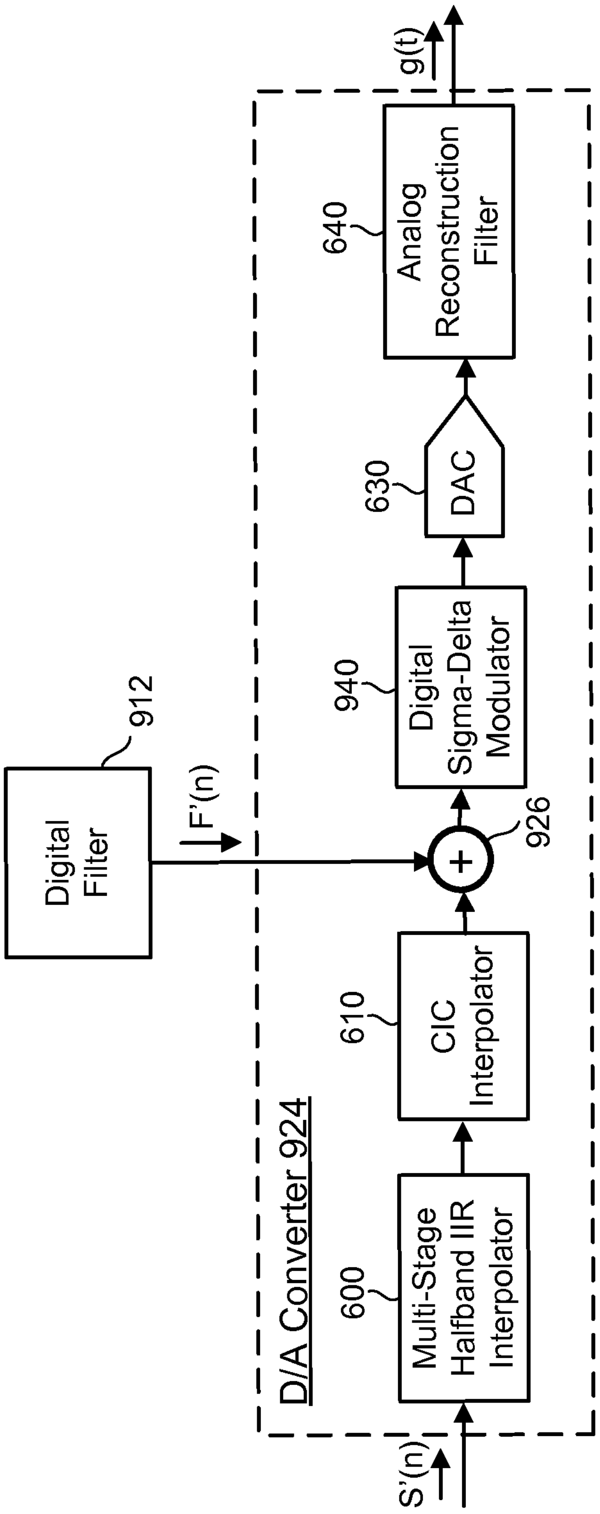
FIG. 9C is a block diagram of an exemplary digital-to-analog converter module in FIG. 9B.

In the low latency ANC processing system 920, the single-bit reduction data stream (F'(n)) generated by the filter 912 is not combined with the interpolated digital desired signal S'(n) prior to being fed into the D/A converter 924. Instead, as shown in the example in FIG. 9C, the single-bit reduction data stream (F'(n)), in FIG. 9B, from digital filter 912 is fed directly into a combiner 926 that combines the single-bit reduction data stream F'(n) with the output of CIC Interpolator 610 of the D/A converter 924. The combined digital signal is fed directly into a specific digital sigma-delta modulator 940 of the D/A converter 924 in the example in FIG. 9C. As such, initial interpolators (see, e.g., elements 600 and 610 in FIG. 9C) are bypassed. The D/A converter module 922 or, more specifically, the D/A converter 924 may be equipped with the specific digital sigma-delta modulator 940 for allowing a single-bit data stream input, which is supplied at relatively high sampling rate. Bypassing one or more initial interpolators of the D/A converter module 922 further allows reducing latency in the overall system.

Figure 10:
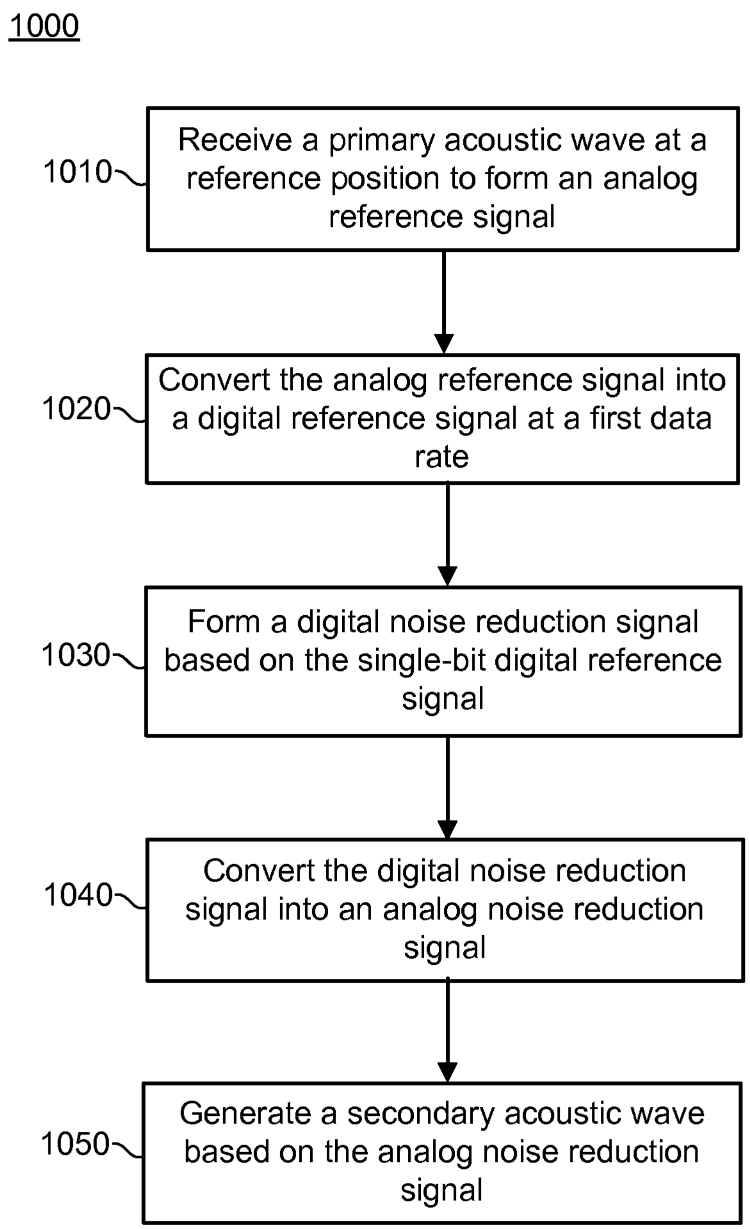
FIG. 10 is a flow chart of another example of performing active noise cancellation.

FIG. 10 is a process flow chart corresponding to method 1000 for performing active noise cancellation, in accordance with certain embodiments. As with all flow charts herein, in some embodiments the steps may be combined, performed in parallel, or performed in a different order. Method 1000 of FIG. 10 may also include more or fewer steps than those illustrated.

In step 1010, the primary acoustic wave is received by the reference microphone 106 to form analog reference signal r(t). In some embodiments, more than one reference signal may be received and processed.

In step 1020, the analog reference signal r(t) is converted into the digital reference signal R(n) using an oversampling data converter. The oversampling data converter produces a single-bit data stream, which is fed directly into a filter. This part of method 1000 differs from the one described above with reference to FIG. 4, in which this single-bit data stream is first fed into a decimator to form decimated digital reference signal R'(n). As stated above, bypassing the decimator allows substantial reduction in latency.

Method 1000 proceeds with step 1030, in which the digital noise reduction signal F'(n) is formed by applying the digital filter to the single-bit digital reference signal. In step 1040, the digital noise reduction signal F'(n) is converted into an analog noise reduction signal to form analog electric signal g(t). In step 1050, the analog electric signal g(t) is then provided to a transducer of the first earpiece of the headset to generate the secondary acoustic wave, thereby performing active noise cancellation at the first listening position.

As used herein, the term "exemplary" means "example" or "illustrative" and does not indicate any preference to use any particular embodiments. Furthermore, a given signal, event, or value is "based on" a predecessor signal, event, or value if the predecessor signal, event, or value influenced the given signal, event, or value. If there is an intervening processing element, step, or time period, the given signal can still be "based on" the predecessor signal, event, or value. If the intervening processing element or step combines more than one signal, event, or value, the output of the processing element or step is considered to be "based on" each of the signal, event, or value inputs. If the given signal, event, or value is the same as the predecessor signal, event, or value, this is merely a degenerate case in which the given signal, event, or value is still considered to be "based on" the predecessor signal, event, or value. "Dependency" on a given signal, event, or value upon another signal, event, or value is defined similarly.

The above described modules may be comprised of instructions that are stored in a storage media such as a machine readable medium (e.g., computer readable medium). These instructions may be retrieved and executed by a processor. Some examples of instructions include software, program code, and firmware. Some examples of storage media comprise memory devices and integrated circuits. The instructions are operational.

While the present invention is disclosed by reference to the preferred embodiments and examples detailed above, it is to be understood that these examples are intended in an illustrative rather than a limiting sense. It is contemplated that modifications and combinations will readily occur to those skilled in the art, and these modifications and combinations will be within the spirit of the invention and the scope of the following claims.

What is claimed is:

1. A method for reducing an acoustic energy level at a listening position, the method comprising:

receiving a primary acoustic wave at a reference position to form an analog reference signal;

converting the analog reference signal into a single-bit digital reference signal using an oversampling data converter;

forming a digital noise reduction signal based on the single-bit digital reference signal using a filter, wherein the filter receives the single-bit digital reference signal directly from the oversampling data converter;

converting the digital noise reduction signal into an analog noise reduction signal; and generating a secondary acoustic wave based on the analog noise reduction signal, the secondary acoustic wave adapted to reduce the acoustic energy level at the listening position.

2. The method of claim 1, wherein the digital noise reduction signal formed by the filter is a single-bit digital noise reduction signal.

3. The method of claim 2, wherein the single-bit digital noise reduction signal is fed directly into a digital-to-analog converter, so as to bypass one or more interpolators thereof, for converting the single-bit digital noise reduction signal into the analog noise reduction signal.

4. The method of claim 1, wherein forming the digital noise reduction signal comprises processing a multiple-bit digital signal generated based on the single-bit digital reference signal during processing of the single-bit digital reference signal.

5. The method of claim 1, wherein the oversampling data converter is a sigma-delta modulator.

6. The method of claim 1, wherein a latency between receiving the primary acoustic wave and generating the secondary acoustic wave is less than or equal to 10 microseconds.

7. The method of claim 1, wherein the primary acoustic wave is received at the reference position by a reference microphone arranged on an earpiece of a headset, and the secondary acoustic wave is generated by an audio transducer arranged on the earpiece.

8. The method of claim 7, further comprising:

receiving the primary acoustic wave and the secondary acoustic wave via a monitoring microphone to form a monitoring signal, the monitoring microphone arranged between the audio transducer and the listening position; and generating the secondary acoustic wave further based on the monitoring signal.

9. A system for reducing an acoustic energy level at a listening position, the system comprising:

a reference microphone configured to receive a primary acoustic wave at the listening position;

a noise cancellation module configured to:

convert an analog reference signal into a single-bit digital reference signal using an oversampling data converter;

form a digital noise reduction signal based on the single-bit digital reference signal using a filter, wherein the filter receives the single-bit digital reference signal directly from the oversampling data converter; and convert the digital noise reduction signal into an analog noise reduction signal; and an audio transducer to generate a secondary acoustic wave based on the analog noise reduction signal, the secondary acoustic wave adapted to reduce the acoustic energy level at the listening position.

10. The system of claim 9, wherein the digital noise reduction signal formed by the filter is a single-bit digital noise reduction signal.

11. The system of claim 10, wherein the single-bit digital noise reduction signal is fed directly into a digital-to-analog converter, so as to bypass one or more interpolators thereof, for converting the single-bit digital noise reduction signal into the analog noise reduction signal.

12. The system of claim 9, wherein forming the digital noise reduction signal comprises processing a multiple-bit digital signal generated based on the single-bit digital reference signal during processing of the single-bit digital reference signal.

13. The system of claim 9, wherein the oversampling data converter is a sigma-delta modulator.

14. The system of claim 9, wherein a latency between receiving the primary acoustic wave and generating the secondary acoustic wave is less than or equal to 10 microseconds.

15. The system of claim 9, wherein the reference microphone and the audio transducer are each arranged on an earpiece of a headset.

16. The system of claim 15, further comprising a monitoring microphone to receive the primary acoustic wave and the secondary acoustic wave to form a monitoring signal, the monitoring microphone arranged between the audio transducer and the listening position; and wherein the noise cancellation module forms the digital noise reduction signal further based on the monitoring signal.

17. A non-transitory computer readable storage medium having embodied thereon a program, the program being executable by a processor to perform a method for reducing an acoustic energy level at a listening position, the method comprising:

receiving a primary acoustic wave at a reference position to form an analog reference signal;

converting the analog reference signal into a single-bit digital reference signal using an oversampling data converter;

forming a digital noise reduction signal based on the single-bit digital reference signal using a filter, wherein the filter receives the single-bit digital reference signal directly from the oversampling data converter;

converting the digital noise reduction signal into an analog noise reduction signal; and generating a secondary acoustic wave based on the analog noise reduction signal, the secondary acoustic wave adapted to reduce the acoustic energy level at the listening position.

18. The non-transitory computer readable storage medium of claim 17, wherein the digital noise reduction signal formed by the filter is a single-bit digital noise reduction signal.

19. The non-transitory computer readable storage medium of claim 18, wherein the single-bit digital noise reduction signal is fed directly into a digital-to-analog converter, so as to bypass one or more interpolators thereof, for converting the single-bit digital noise reduction signal into the analog noise reduction signal.

20. The non-transitory computer readable storage medium of claim 17, wherein forming the digital noise reduction signal comprises processing a multiple-bit digital signal generated based on the single-bit digital reference signal during processing of the single-bit digital reference signal.

* * * * *